United States Patent [19]

Markowitz

[11] 4,421,116
[45] Dec. 20, 1983

[54] HEART PACEMAKER WITH SEPARATE A-V INTERVALS FOR ATRIAL SYNCHRONOUS AND ATRIAL-VENTRICULAR SEQUENTIAL PACING MODES

[75] Inventor: H. Toby Markowitz, Anoka, Minn.

[73] Assignee: Medtronic, Inc., Minneapolis, Minn.

[21] Appl. No.: 356,791

[22] Filed: Mar. 10, 1982

Related U.S. Application Data

[63] Continuation of Ser. No. 196,473, Oct. 14, 1980, abandoned.

[51] Int. Cl.³ ............................................. A61N 1/36
[52] U.S. Cl. ............................................. 128/419 PG
[58] Field of Search ................................. 128/419 PG

[56] References Cited

U.S. PATENT DOCUMENTS 3,557,796  1/1971  Keller, Jr. et al. ............ 128/419 PG

FOREIGN PATENT DOCUMENTS 2701104  7/1978  Fed. Rep. of Germany ...... 128/419 PG Primary Examiner—William E. Kamm
Attorney, Agent, or Firm—Merchant, Gould, Smith, Edell, Welter & Schmidt

[57] ABSTRACT

A dual chamber heart pacemaker has atrial and ventricular pulse generators (21, 22) and sense amplifiers (25, 26) which connect respectively to an atrial terminal (11) and a ventricular terminal (12) for connection to the heart. In an atrial synchronous mode, the pacemaker provides ventricular stimulating pulses in response to detected spontaneous atrial contractions, and spaced from them by an A-V interval determined by a timer (31). In an atrial-ventricular sequential mode, a timer (40) causes the pacemaker to deliver sequential atrial and ventricular stimulation pulses which are separated in time by an A-V interval determined by another timer (30). The atrial-ventricular intervals for atrial synchronous mode and atrial-ventricular sequential mode are independent of each other, permitting selection of different A-V intervals for the two modes of operation.

6 Claims, 1 Drawing Figure

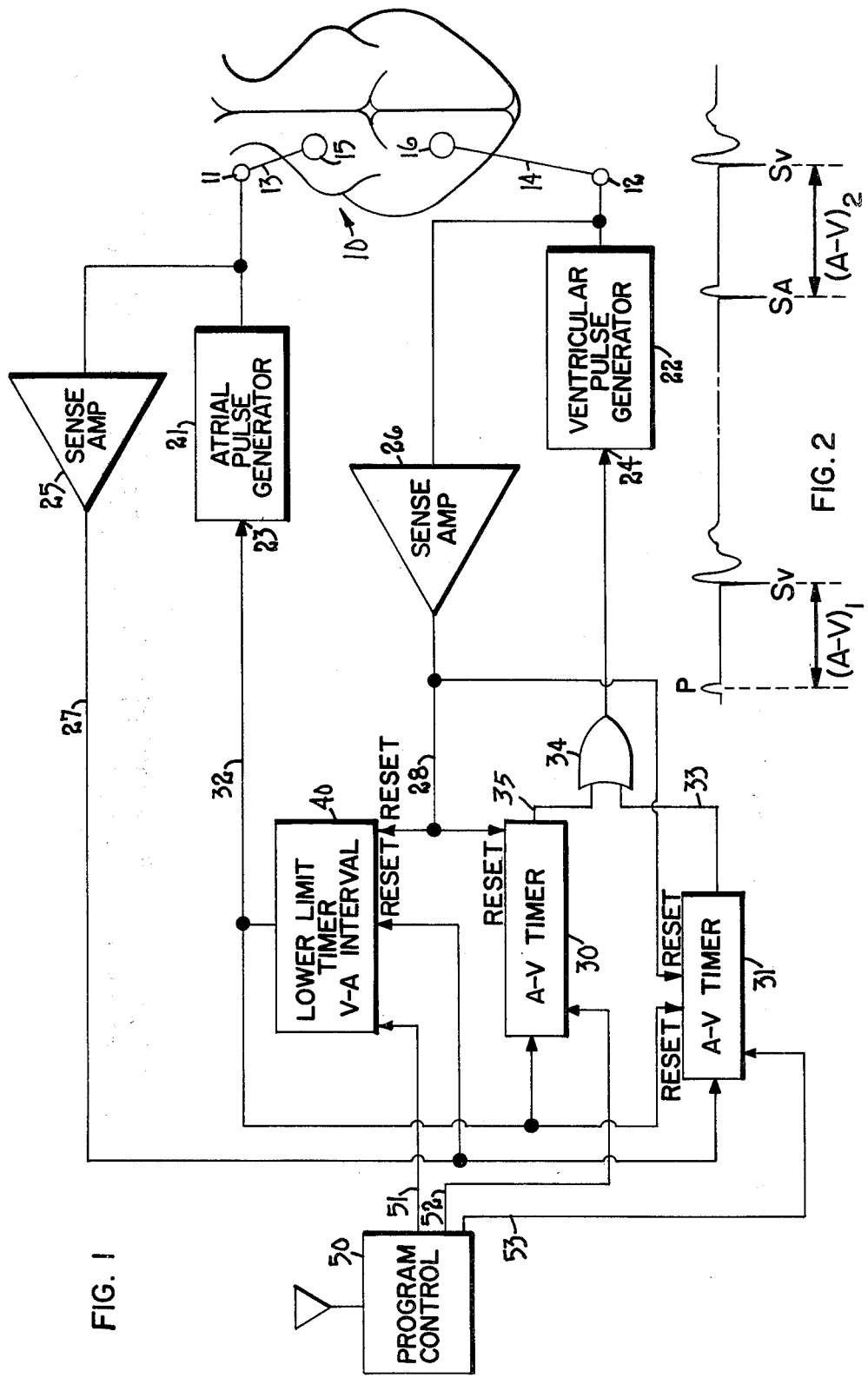

HEART PACEMAKER WITH SEPARATE A-V INTERVALS FOR ATRIAL SYNCHRONOUS AND ATRIAL-VENTRICULAR SEQUENTIAL PACING MODES

This is a continuation of application Ser. No. 196,473, filed Oct. 14, 1980, now abandoned.

FIELD OF THE INVENTION

This invention pertains to the field of artificial heart pacemakers designed to provide stimulating electrical pulses to the heart of a patient. More specifically, the invention pertains to improvements in dual chamber type pacemakers, by providing different atrial-ventricular delay intervals for different modes of operation of the pacemaker.

Dual chamber pacemakers include those heart pacemakers which have means for both stimulating and sensing in both the atrium and ventricle of the heart. This type of pacemaker is intended for use with electrode leads attached to, or in, both the atrium and the ventricle. Pulse generating circuits are provided in the pacemaker for selectively delivering electrical stimulation pulses to the atrium and ventricle, respectively. Sense amplifiers are provided connected to the atrial and ventricular leads for sensing, respectively, P-waves indicative of atrial depolarizations or contractions, and R-waves indicative of ventricular depolarizations or contractions. Control circuitry is provided for operating in different modes, including atrial synchronous and atrial-ventricular sequential modes of operation.

The atrial synchronous mode is established when the patient's heart has a spontaneous or naturally occurring atrial depolarization at the appropriate time in the heartbeat cycle. This atrial depolarization is sensed by the atrial sense amplifier, and a time delay is initiated within the pacemaker, referred to as the atrial-ventricular time delay, or the P-R interval, with a ventricular stimulation pulse to be delivered at the end of that interval. The A-V delay interval is to generally correspond to normal A-V intervals occurring in the normal synchronized atrial and ventricular contractions of the heart. If a ventricular depolarization takes place during the timing of the A-V interval, as by normal conduction in the heart, the R-wave will be sensed by the ventricular sensing amplifier and the pacemaker pulse generating and timing circuits will be reset or inhibited so that no ventricular stimulation pulse will be delivered for that cycle.

The atrial-ventricular sequential mode occurs when a spontaneous atrial depolarization does not take place within the appropriate time interval from a preceding heartbeat in accordance with a selected minimum heart rate. In that event an atrial stimulation pulse is delivered and timing circuitry within the pacemaker is provided to generate an atrial-ventricular time delay interval, at a completion of which a ventricular stimulation pulse is to be delivered. In one type of pacemaker, if a spontaneous ventricular contraction, or a premature ventricular contraction (PVC) takes place during this A-V interval, its R-wave will be sensed by the ventricular sense amplifier and the ventricular output circuits will be inhibited. Other types of pacemakers referred to as "committed" pacemakers are designed to deliver the ventricular stimulating pulse at the end of the A-V interval from the atrial stimulation pulse, without regard to whether there is any ventricular activity during this interval. These types of pacemakers include unipolar devices in which the ventricular sensing amplifier is blanked or rendered insensitive following the delivery of the atrial stimulation pulse for a blanking period that covers the A-V interval, so that the ventricular sensing amplifier is not capable of sensing ventricular depolarizations or PVCs during that interval.

In prior art programmable pacemakers, the A-V delay interval along with various other operating parameters of the pacemaker may be selected or programmed by means of an external programmer as is generally known in the art. However, the A-V delay interval, once programmed, is the same for atrial synchronous and atrial-ventricular sequential pacing modes.

The present invention provides significant improvements in performance and operating flexibility for dual chamber pacemakers by providing separate atrial-ventricular time delays in atrial synchronous and atrial-ventricular sequential pacing modes. In addition, both A-V delay intervals can be made programmable, for use in a programmable-type pacemaker. The manner in which this is done according to the present invention is set forth in greater detail below with specific reference to the drawings. However, the important advantages which result from the invention are as follows.

One advantage of the present invention is to provide the patient with a longer A-V delay interval while the patient is at rest, and a shorter A-V delay interval when at exercise. This is useful for patients with exercise induced block. For this type of case the A-V interval for A-V sequential pacing can be made longer than the A-V interval for atrial synchronous pacing. The minimum rate of the device can be set so that when the patient is at rest the pacemaker is operating in A-V sequential inhibited mode. The longer A-V interval in this mode allows for normal A-V conduction within the patient's heart. When the patient is at exercise with a high atrial rate above the minimum rate of the device but with the exercise induced block, the device will operate in atrial synchronous mode, and the short A-V interval provided for this mode will not provide a hemodynamic compromise at high heartbeat rates associated with the exercise.

Another advantage that may be realized by the separate A-V delays provided by this invention is to aid in ECG interpretation. Presently, the surface ECG of a patient with a dual chamber pacemaker appears to show different A-V delays for atrial synchronous and atrial-ventricular sequential pacing, even though the identical A-V time interval is used in the pacemaker. This apparent difference is due to the effects of lead location and propagation time within the heart to the lead, together with sense amplifier delays, and the net effect of these delays is to make the A-V delay following an atrial sense appear to be longer than the A-V delay between sequential A and V pacing spikes. However, in the present invention, by making the A-V delay for sequential pacing longer than the A-V delay for atrial synchronous pacing, the apparent delays as seen in the surface ECG may appear to be the same, thus helping to avoid unnecessary confusion by medical personnel in interpreting the ECG.

A further advantage of the separate A-V delays according to the present invention is in the case of committed A-V sequential devices, such as unipolar systems that require blanking of the ventricular sense amplifier during and after the atrial stimulating pulse. Such systems are committed to delivering the ventricular stimulating pulse in sequence after the atrial stimulating pulse, regardless of whether any ventricular activity takes place during the A-V delay. With these types of pacemakers, it is necessary to limit the A-V delay to approximately 150 milliseconds as a safety precaution to guard against delivering the ventricular stimulation pulse during the vulnerable period of the ventricles in the event of the occurrence of an unsensed premature ventricular contraction (PVC) occurring after the atrial stimulus during the A-V interval. It is generally accepted that holding the A-V delay to 150 milliseconds will avoid the initiation of ventricular tachycardia. However, for other considerations it would be desirable to have an A-V interval longer than 150 milliseconds, but this was not possible in prior art committed or unipolar sequential pacemakers because of the above-noted problem.

However, the present invention permits use of a relatively short, safe A-V delay such as 150 milliseconds for A-V sequential pacing to preserve the safety factor, while providing a second A-V delay during atrial synchronous pacing. This second A-V delay can be made either shorter or longer, or it can be programmable. For example, it can be made longer, in the range of 175-200 milliseconds in order to allow for normal conduction in the heart and more efficient pumping action.

SUMMARY OF THE INVENTION

According to the present invention there is provided an improved heart pacemaker which includes atrial and ventricular terminals for connection respectively to the atrium and ventricle of a patient's heart. Atrial and ventricular pulse generating circuits are provided and are selectively operative for delivering stimulating pulses to the atrial and ventricular terminals. Atrial sensing means are connected to the atrial terminal for sensing P-waves indicative of atrial contractions of the patient's heart, and preferably ventricular sensing means are connected for sensing R-waves indicative of ventricular contractions of the patient's heart.

Timing control means are operatively connected to the atrial sensing means and the atrial and ventricular pulse generating means, the timing control means being operative in response to a sensed atrial contraction to cause the ventricular pulse generating means to deliver a stimulating pulse at the end of a first A-V delay interval from the sensed atrial contraction, and operative in the absence of sensed atrial contractions to cause the atrial and ventricular pulse generating means to deliver sequential stimulating pulses at a predetermined pacing rate, with the atrial and ventricular sequential pulses being separated in time by a second A-V delay interval which is independent of said first A-V delay interval.

BRIEF DESCRIPTION OF THE DRAWING

In the drawing, FIG. 1 is a block diagram of a heart pacemaker according to the present invention and;

FIG. 2 is a graph showing pertinent wave forms illustrating the operation of the pacemaker of FIG. 1.

DETAILED DESCRIPTION OF THE PREFERRED EMBODIMENT

In FIG. 1, a dual chamber pacemaker incorporating the present invention is shown in block diagram form. Reference number 10 generally designates a human heart with which the pacemaker would be used. The various circuits of the pacemaker are represented by the blocks. The pacemaker connects from an atrial terminal 11 and a ventricular terminal 12 to the atrium and ventricle of the heart, by means of atrial lead 13 and ventricular lead 14, respectively. Electrodes 15 and 16 are provided at the ends of leads 13 and 14, respectively, for making electrical contact with the tissues on or in the corresponding chamber of the heart.

The circuits within the pacemaker include atrial pulse generator 21 and ventricular pulse generator 22. The electrical designs of these circuits are conventional and are therefore not shown in detail. These pulse generators operate in response to pace or trigger signals applied at their inputs, 23, 24 respectively. The stimulation pulses from their outputs connect respectively to atrial terminal 11 and ventricular terminal 12. The atrial sensing amplifier 25 has its input also connected to terminal 11, and its output connected to conductor 27. Ventricular sensing amplifier 26 is connected with its input to terminal 12, and its output to conductor 28. Sense amplifiers 25 and 26 are provided with appropriate amplifying and filtering circuits as are generally known in the art, for detecting respectively the P-waves indicative of atrial depolarizations in the case of amplifier 25, and R-waves indicative of ventricular depolarizations, in the case of amplifier 26. In either case an appropriate signal is generated at lead 27 or 28 to indicate the detection of a P-wave or R-wave respectively.

In the embodiment shown in FIG. 1, a pair of atrial-ventricular delay timers are provided, indicated by reference numbers 30 and 31. A-V timer 31 has an input which connects to conductor 27, an output which connects to conductor 33, and a pair of reset inputs which connect to branches of conductors 28 and 32, respectively. Timer 31 functions to initiate the timing of a delay interval upon receipt of a signal at its input from atrial sensing amplifier 25, and to provide a trigger signal at its output on conductor 33 at the completion or time-out of the A-V interval. Conductor 33 connects as one input to an OR gate 34, the output of which connects to input 24 of the ventricular pulse generator 22.

A-V timer 30 is similar to A-V timer 31 described above, except that it has its own time interval independent of the other timer, the value of which could be shorter, longer or the same as that for timer 31. Timer 30 receives its start signal from conductor 32, and at the end of its time-out interval provides a trigger signal at conductor 35, which connects as the other input to OR gate 34. Timer 30 has a reset input connected to a branch of conductor 28.

A timer control 40 is provided for timing and initiating A-V sequential pacing if the spontaneous atrial rate of the patient drops below a lower limit set by timer 40. Timer 40 has an output which connects to conductor 32, a branch of which connects to the trigger input 23 of atrial pulse generator 21. As previously mentioned, other branches of conductor 32 connect to the input of A-V timer 30, and to a reset input of timer 31.

Conductor 28, which receives the output signals from sense amplifier 26, connects to reset inputs of lower limit timer 40, A-V timer 30 and A-V timer 31.

When used in conjunction with a programmable pacemaker, any or all of timers 40, 30 and 31 can be programmable. As indicated in FIG. 1, a program control device 50 receives RF signals from a programmer external to the pacemaker, in a manner generally known in the art. Program control 50 may send programming signals over conductor 51 to a program input of timer 40. Similarly, conductors 52 and 53 may convey program signals to timers 30 and 31, if desired. Timers 40, 30 and 31 may be designed using known analog or digital techniques so that programming inputs may change or program different time delays. As previously mentioned, depending on the application, it may be desirable to leave one or more of the timers with a fixed interval, while one or more of the others are programmable, but FIG. 1 shows all three being programmable because this may be done in the broadest sense.

The pacemaker of FIG. 1 responds with atrial synchronous pacing in response to atrial contractions at above the lower rate limit. An atrial contraction is detected by sense amplifier 25, and a signal at conductor 27 causes A-V timer 31 to initiate its time period. At the same time timer 40 is reset to prevent generation of an atrial stimulation pulse. Assuming no ventricular event takes place in the interim, when A-V timer 31 times out its interval, a trigger signal is conveyed through gate 34 to cause ventricular pulse generator 22 to deliver its ventricular stimulating pulse. This stimulation will be synchronized with the originating atrial contraction and separated from it by the A-V interval of timer 31. If a ventricular depolarization takes place during the interval of timer 31, as for example by normal conduction through the heart, it will be detected by sense amplifier 26, resulting in the reset of timer 31 so that no ventricular pulse will be delivered.

In case the atrial contractions are lacking, or are occurring at too low a rate, timer 40 will initiate atrial-ventricular sequential pacing. Timer 40 is reset by sense amplifier 26 upon occurrence of a ventricular event, either a spontaneous ventricular contraction of a ventricular stimulation pulse. It then begins to time out its interval. If not reset by the occurrence of a spontaneous atrial pulse, timer 40 will put out a signal on conductor 32 at the end of its interval to trigger atrial pulse generator 21 to generate an atrial stimulation pulse. At the same time the signal on conductor 32 will trigger A-V timer 30 to initiate its time-out interval, and will cause timer 31 to be reset. At the end of its time-out interval, timer 30 will send a triggering signal through OR gate 34 to cause ventricular pulse generator 22 to deliver a ventricular stimulation pulse following the atrial stimulation pulse by the A-V delay of timer 30. The design of timer 31 is such that a reset signal received from conductor 32 effectively holds timer 31 reset long enough to prevent it from being triggered by the atrial stimulation pulse caused by timer 40, which will be detected by sense amplifier 25. This prevents timer 31 from competing with timer 30 in the event that timer 31 has a shorter A-V interval than timer 30.

Any time a ventricular depolarization takes place it is sensed by sense amplifier 26, and timers 40, 30 and 31 are reset. Thus, if a ventricular depolarization takes place through normal heart conduction following an atrial stimulated pulse, during the time that A-V timer 30 is timing-out its interval, it will be reset so that no ventricular stimulating pulse will be delivered.

Referring to FIG. 2, a simplified waveform is shown illustrating the operation of the pacemaker of FIG. 1 in both atrial synchronous and atrial-ventricular sequential pacing. In FIG. 2, the first waveform complex illustrates an instance of atrial synchronous pacing. An atrial depolarization occurs, as indicated by the first P-wave in FIG. 2. This activates A-V timer 31 of FIG. 2, and at the end of its delay, indicated in FIG. 2 as $(A-V)_1$, a ventricular stimulation pulse is delivered, causing a ventricular depolarization.

Assume now for purposes of illustration that a spontaneous P-wave does not occur soon enough after the ventricular depolarization to meet the minimum rate requirements of the device. Timer 40 of FIG. 1 then times out its interval and delivers an atrial stimulating pulse, $S_A$. At the same time A-V timer 30 is activated, and at the end of its time-out period, $(A-V)_2$ assuming no spontaneous ventricular depolarization, the ventricular stimulating pulse, indicated as $S_V$ is delivered. The two A-V delays for the atrial synchronous and atrial-ventricular sequential pacing are of different lengths.

What is claimed is:

1. A heart pacemaker, comprising:
   atrial and ventricular terminal means for connection respectively to the atrium and ventricle of a patient's heart;
   atrial and ventricular pulse generating means connected for selectively delivering stimulating pulses to said atrial and ventricular terminal means;
   atrial sensing means connected to said atrial terminal means, and operative for sensing atrial contractions of the patient's heart; and
   timing control means operatively connected to said atrial sensing means and said atrial and ventricular pulse generating means, and operative in response to a sensed atrial contraction to cause said ventricular pulse generating means to deliver a stimulating pulse at the end of a first atrial-ventricular delay interval from said sensed atrial contraction, and operative in the absence of sensed atrial contractions to cause said atrial and ventricular pulse generating means to deliver sequential stimulating pulses at a predetermined pacing rate, with said atrial and ventricular sequential pulses being separated in time by a second atrial-ventricular delay interval which is independent of said first atrial-ventricular delay interval.

2. A heart pacemaker, comprising:
   atrial and ventricular terminal means for connection to the atrium and ventricle, respectively, of a patient's heart;
   atrial pulse generating means for selectively delivering stimulating pulses to said atrial terminal means;
   ventricular pulse generating means for selectively delivering stimulating pulses to said ventricular terminal means;
   atrial sensing means connected to said atrial terminal means, for sensing atrial contractions of the patient's heart;
   first atrial-ventricular delay timer means, operatively connected to said atrial sensing means and operatively connected for causing said ventricular pulse generating means to deliver stimulating pulse after an atrial-ventricular time delay following a sensed atrial contraction;
   low rate limit timer means operative, in the absence of a sensed atrial contraction, to cause said atrial pulse generating means to deliver a stimulating pulse at the end of a predetermined time interval from a previous ventricular stimulating pulse; and
   second atrial-ventricular time delay means operatively connected for actuation in the event of an atrial stimulation pulse caused by said lower rate limit timer, and operatively connected for causing said ventricular pulse generator to deliver a ventricular stimulation pulse following a second atrial-ventricular time delay from said atrial stimulation pulse, where said second time delay is longer than said first time delay.

3. A pacemaker according to claim 2 further including ventricular sensing means for sensing ventricular contractions of the patient's heart and wherein said lower rate limit timer is adapted for timing its predetermined time period from a sensed or stimulated ventricular contraction.

4. A heart pacemaker according to claim 3 wherein said ventricular sensing means is operatively connected to said lower rate limit timer and said first and second atrial-ventricular delay timers for resetting each of said timers in response to a sensed or stimulated ventricular contraction.

5. A heart pacemaker according to claim 2 including means for programing said first atrial-ventricular delay timer for programing the duration of said first time delay.

6. A heart pacemaker according to claim 5 further including programing means connected for programing said second atrial-ventricular delay timer for programing said second time delay.

* * * * *